US011273137B2

(12) United States Patent
Bachmann et al.

(10) Patent No.: US 11,273,137 B2
(45) Date of Patent: Mar. 15, 2022

(54) METHODS AND COMPOSITIONS TO PREVENT AND TREAT DISORDERS ASSOCIATED WITH MUTATIONS IN THE ODC1 GENE

(71) Applicants: Board of Trustees of Michigan State University, East Lansing, MI (US); Spectrum Health Innovations LLC, Grand Rapids, MI (US)

(72) Inventors: Andre Bachmann, Grand Rapids, MI (US); Caleb Bupp, Grand Rapids, MI (US); Surender Rajasekaran, Grand Rapids, MI (US)

(73) Assignees: Board of Trustees of Michigan State University, East Lansing, MI (US); Spectrum Health Innovations LLC, Grand Rapids, MI (US)

( * ) Notice: Subject to any disclaimer, the term of this patent is extended or adjusted under 35 U.S.C. 154(b) by 16 days.

(21) Appl. No.: 16/560,026

(22) Filed: Sep. 4, 2019

(65) Prior Publication Data
US 2020/0215010 A1 Jul. 9, 2020

Related U.S. Application Data

(60) Provisional application No. 62/726,754, filed on Sep. 4, 2018.

(51) Int. Cl.
| | |
|---|---|
| *A61K 31/195* | (2006.01) |
| *A61K 31/198* | (2006.01) |
| *A61K 31/155* | (2006.01) |
| *A61K 31/4418* | (2006.01) |
| *A61K 31/132* | (2006.01) |
| *A61K 31/16* | (2006.01) |
| *A61K 31/137* | (2006.01) |
| *A61K 31/4412* | (2006.01) |
| *A61K 45/06* | (2006.01) |

(52) U.S. Cl.
CPC .......... *A61K 31/198* (2013.01); *A61K 31/132* (2013.01); *A61K 31/137* (2013.01); *A61K 31/155* (2013.01); *A61K 31/16* (2013.01); *A61K 31/4412* (2013.01); *A61K 31/4418* (2013.01); *A61K 45/06* (2013.01)

(58) Field of Classification Search
CPC .................................................. A61K 31/198
USPC ......................................................... 514/564
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |

(Continued)

FOREIGN PATENT DOCUMENTS

| | | |
|---|---|---|
| WO | WO-2009/008725 A2 | 1/2009 |
| WO | WO-2013/112053 A1 | 8/2013 |

OTHER PUBLICATIONS

Somani et al. "Ornithine decarboxylase inhibition: Astrategy to combat various disease," Mino Rev. Med Chem, Jun. 2018, vol. 18, No. 12, pp. 1008-1021, abstract, https://www.eurekaselect.com/155910/article (Year: 2018).*

(Continued)

*Primary Examiner* — Shengjun Wang
(74) *Attorney, Agent, or Firm* — Foley Hoag LLP

(57) ABSTRACT

The invention provides methods for treating or preventing developmental disorders associated with mutations in the OCD1 gene.

2 Claims, 4 Drawing Sheets
Specification includes a Sequence Listing.

(56) References Cited

U.S. PATENT DOCUMENTS

| | | | |
|---|---|---|---|
| 4,837,028 | A | 6/1989 | Allen |
| 5,019,369 | A | 5/1991 | Presant et al. |
| 5,539,082 | A | 7/1996 | Nielsen et al. |
| 5,714,331 | A | 2/1998 | Buchardt et al. |
| 5,719,262 | A | 2/1998 | Buchardt et al. |
| 6,670,461 | B1 | 12/2003 | Wengel et al. |
| 6,794,499 | B2 | 9/2004 | Wengel et al. |
| 6,969,766 | B2 | 11/2005 | Kim et al. |
| 7,022,851 | B2 | 4/2006 | Kim et al. |
| 7,034,133 | B2 | 4/2006 | Wengel et al. |
| 7,053,207 | B2 | 5/2006 | Wengel |
| 7,060,809 | B2 | 6/2006 | Wengel et al. |
| 7,084,125 | B2 | 8/2006 | Wengel |
| 7,125,994 | B2 | 10/2006 | Kim et al. |
| 7,145,006 | B2 | 12/2006 | Kim et al. |
| 7,179,896 | B2 | 2/2007 | Kim et al. |
| 7,211,668 | B2 | 5/2007 | Kim et al. |
| 7,569,575 | B2 | 8/2009 | Sorensen et al. |
| 7,572,582 | B2 | 8/2009 | Wengel et al. |
| 8,268,798 | B2 | 9/2012 | Chatterton |
| 8,313,772 | B2 | 11/2012 | Rozema et al. |
| 8,324,366 | B2 | 12/2012 | Akinc et al. |
| 8,426,554 | B2 | 4/2013 | Rozema et al. |
| 8,501,930 | B2 | 8/2013 | Rozema et al. |
| 9,072,788 | B2 | 7/2015 | Blumberg et al. |
| 2010/0120727 | A1 | 5/2010 | Xu |
| 2011/0071208 | A1 | 3/2011 | MacLachlan et al. |
| 2020/0215010 | A1 | 7/2020 | Bachmann et al. |

OTHER PUBLICATIONS

Loguidice et al. (Alpha-Difluoromethyllornithine, an irreversible inhibitor of polyamine biosynthesis, as a therapeutic strategy against hyperproliterative and infectious diseases, Medical Sciences, Feb. 2018, 6, 12 https://www.ncbi.nlm.nih.gov/pmc/articles/PMC5872169/pdf/medsci-06-00012.pdf (Year: 2018).*

Soler et al. "Modulation of murine hair follicle function by alterations in ornithine decarboxylase activity," J. Investigative Dermatology, 1996, vol. 106, No. 5, pp. 1108-1113 (Year: 1996).*

Megosh et al. "Increased frequency of spontaneous skin tumor in transgenic mice which overexpress ornithine decarboxylase," Cancer Research, 1995, vol. 55, pp. 4205-4209 (Year: 1995).*

Bernstein et al. "The cellular localization of the L-ornithine decarboxylase/polyamine system in normal and diseased central nervous systems," Progress in Neurobiology, 1999, vol. 57, pp. 485-505 (Year: 1999).*

Gaj et al., "ZFN, TALEN, and CRISPR/Cas-based methods for genome engineering," Cell, 31(7): 397-405 (2013).

Hyvonen et al., "Assay of Ornithine Decarboxylase and Spermidine/Spermine N1-acetyltransferase Activities," Bio-Protocol, 4(22): e1301 (2014).

Kawata et al., "Administration of PLK-1 small interfering RNA with atelocollagen prevents the growth of liver metastases of lung cancer," Molecular Cancer Therapeutics, 7(9): 2904-2912 (2008).

Zhang et al., "Multiplex Genome Engineering Using CRISPR/Cas Systems," Science, 339(6121): 819-823 (2013).

* cited by examiner

SEQUENCE LISTING

<160> NUMBER OF SEQ ID NOS: 3

<210> SEQ ID NO 1
<211> LENGTH: 1386
<212> TYPE: DNA
<213> ORGANISM: Homo sapiens

<400> SEQUENCE: 1

| | |
|---|---|
| atgaacaact ttggtaatga agagtttgac tgccacttcc tcgatgaagg ttttactgcc | 60 |
| aaggacattc tggaccagaa aattaatgaa gtttcttctt ctgatgataa ggatgccttc | 120 |
| tatgtggcag acctgggaga cattctaaag aaacatctga ggtggttaaa agctctccct | 180 |
| cgtgtcaccc ccttttatgc agtcaaatgt aatgatagca aagccatcgt gaagacccct | 240 |
| gctgctaccg ggacaggatt tgactgtgct agcaagactg aaatacagtt ggtgcagagt | 300 |
| ctggggggtgc ctccagagag gattatctat gcaaatcctt gtaaacaagt atctcaaatt | 360 |
| aagtatgctg ctaataatgg agtccagatg atgacttttg atagtgaagt tgagttgatg | 420 |
| aaagttgcca gcacacatcc caaagcaaag ttggttttgc ggattgccac tgatgattcc | 480 |
| aaagcagtct gtcgtctcag tgtgaaattc ggtgccacgc tcagaaccag caggctcctt | 540 |
| ttggaacggg cgaaagagct aaatatcgat gttgttggtg tcagcttcca tgtaggaagc | 600 |
| ggctgtaccg atcctgagac cttcgtgcag gcaatctctg atgcccgctg tgtttttgac | 660 |
| atggggggctg aggttggttt cagcatgtat ctgcttgata ttggcggtgg ctttcctgga | 720 |
| tctgaggatg tgaaacttaa atttgaagag atcaccggcg taatcaaccc agcgttggac | 780 |
| aaatactttc cgtcagactc tggagtgaga atcatagctg agcccggcag atactatgtt | 840 |
| gcatcagctt tcacgcttgc agttaatatc attgccaaga aattgtatt aaaggaacag | 900 |
| acgggctctg atgacgaaga tgagtcgagt gagcagacct ttatgtatta tgtgaatgat | 960 |
| ggcgtctatg gatcatttaa ttgcatactc tatgaccacg cacatgtaaa gccccttctg | 1020 |
| caaaagagac taaaccaga tgagaagtat tattcatcca gcatatgggg accaacatgt | 1080 |
| gatggcctcg atcggattgt tgagcgctgt gacctgcctg aaatgcatgt gggtgattgg | 1140 |
| atgctctttg aaaacatggg cgcttacact gttgctgctg cctctacgtt caatggcttc | 1200 |
| cagaggccga cgatctacta tgtgatgtca gggcctgcgt ggcaactcat gcagcaattc | 1260 |
| cagaaccccg acttcccacc cgaagtagag gaacaggatg ccagcacccct gcctgtgtct | 1320 |
| tgtgcctggg agagtgggat gaaacgccac agagcagcct gtgcttcggc tagtattaat | 1380 |
| gtgtag | 1386 |

<210> SEQ ID NO 2
<211> LENGTH: 1386
<212> TYPE: DNA
<213> ORGANISM: Homo sapiens

<400> SEQUENCE: 2

| | |
|---|---|
| atgaacaact ttggtaatga agagtttgac tgccacttcc tcgatgaagg ttttactgcc | 60 |
| aaggacattc tggaccagaa aattaatgaa gtttcttctt ctgatgataa ggatgccttc | 120 |
| tatgtggcag acctgggaga cattctaaag aaacatctga ggtggttaaa agctctccct | 180 |
| cgtgtcaccc ccttttatgc agtcaaatgt aatgatagca aagccatcgt gaagacccct | 240 |
| gctgctaccg ggacaggatt tgactgtgct agcaagactg aaatacagtt ggtgcagagt | 300 |
| ctggggggtgc ctccagagag gattatctat gcaaatcctt gtaaacaagt atctcaaatt | 360 |
| aagtatgctg ctaataatgg agtccagatg atgacttttg atagtgaagt tgagttgatg | 420 |

-continued

```
aaagttgcca gagcacatcc caaagcaaag ttggttttgc ggattgccac tgatgattcc    480
aaagcagtct gtcgtctcag tgtgaaattc ggtgccacgc tcagaaccag caggctcctt    540
ttggaacggg cgaaagagct aaatatcgat gttgttggtg tcagcttcca tgtaggaagc    600
ggctgtaccg atcctgagac cttcgtgcag gcaatctctg atgcccgctg tgtttttgac    660
atgggggctg aggttggttt cagcatgtat ctgcttgata ttggcggtgg ctttcctgga    720
tctgaggatg tgaaacttaa atttgaagag atcaccggcg taatcaaccc agcgttggac    780
aaatactttc cgtcagactc tggagtgaga atcatagctg agcccggcag atactatgtt    840
gcatcagctt tcacgcttgc agttaatatc attgccaaga aaattgtatt aaaggaacag    900
acgggctctg atgacgaaga tgagtcgagt gagcagacct ttatgtatta tgtgaatgat    960
ggcgtctatg gatcatttaa ttgcatactc tatgaccacg cacatgtaaa gccccttctg    1020
caaaagagac ctaaaccaga tgagaagtat tattcatcca gcatatgggg accaacatgt    1080
gatggcctcg atcggattgt tgagcgctgt gacctgcctg aaatgcatgt gggtgattgg    1140
atgctctttg aaaacatggg cgcttacact gttgctgctg cctctacgtt caatggcttc    1200
cagaggccga cgatctacta tgtgatgtca gggcctgcgt ggcaactcat gcagcaattc    1260
cagaaccccg acttcccacc cgaagtagag gaacaggatg ccagcaccct gcctgtgtct    1320
tgtgcctggg agagtgggat gtaacgccac agagcagcct gtgcttcggc tagtattaat    1380
gtgtag                                                                1386
```

<210> SEQ ID NO 3
<211> LENGTH: 461
<212> TYPE: PRT
<213> ORGANISM: Homo sapiens

<400> SEQUENCE: 3

```
Met Asn Asn Phe Gly Asn Glu Glu Phe Asp Cys His Phe Leu Asp Glu
1               5                   10                  15

Gly Phe Thr Ala Lys Asp Ile Leu Asp Gln Lys Ile Asn Glu Val Ser
            20                  25                  30

Ser Ser Asp Asp Lys Asp Ala Phe Tyr Val Ala Asp Leu Gly Asp Ile
        35                  40                  45

Leu Lys Lys His Leu Arg Trp Leu Lys Ala Leu Pro Arg Val Thr Pro
    50                  55                  60

Phe Tyr Ala Val Lys Cys Asn Asp Ser Lys Ala Ile Val Lys Thr Leu
65                  70                  75                  80

Ala Ala Thr Gly Thr Gly Phe Asp Cys Ala Ser Lys Thr Glu Ile Gln
                85                  90                  95

Leu Val Gln Ser Leu Gly Val Pro Pro Glu Arg Ile Ile Tyr Ala Asn
            100                 105                 110

Pro Cys Lys Gln Val Ser Gln Ile Lys Tyr Ala Ala Asn Asn Gly Val
        115                 120                 125

Gln Met Met Thr Phe Asp Ser Glu Val Glu Leu Met Lys Val Ala Arg
    130                 135                 140

Ala His Pro Lys Ala Lys Leu Val Leu Arg Ile Ala Thr Asp Asp Ser
145                 150                 155                 160

Lys Ala Val Cys Arg Leu Ser Val Lys Phe Gly Ala Thr Leu Arg Thr
                165                 170                 175

Ser Arg Leu Leu Leu Glu Arg Ala Lys Glu Leu Asn Ile Asp Val Val
            180                 185                 190
```

```
Gly Val Ser Phe His Val Gly Ser Gly Cys Thr Asp Pro Glu Thr Phe
        195                 200                 205
Val Gln Ala Ile Ser Asp Ala Arg Cys Val Phe Asp Met Gly Ala Glu
        210                 215                 220
Val Gly Phe Ser Met Tyr Leu Leu Asp Ile Gly Gly Gly Phe Pro Gly
225                 230                 235                 240
Ser Glu Asp Val Lys Leu Lys Phe Glu Glu Ile Thr Gly Val Ile Asn
                245                 250                 255
Pro Ala Leu Asp Lys Tyr Phe Pro Ser Asp Ser Gly Val Arg Ile Ile
                260                 265                 270
Ala Glu Pro Gly Arg Tyr Tyr Val Ala Ser Ala Phe Thr Leu Ala Val
        275                 280                 285
Asn Ile Ile Ala Lys Lys Ile Val Leu Lys Glu Gln Thr Gly Ser Asp
        290                 295                 300
Asp Glu Asp Glu Ser Ser Glu Gln Thr Phe Met Tyr Tyr Val Asn Asp
305                 310                 315                 320
Gly Val Tyr Gly Ser Phe Asn Cys Ile Leu Tyr Asp His Ala His Val
                325                 330                 335
Lys Pro Leu Leu Gln Lys Arg Pro Lys Pro Asp Glu Lys Tyr Tyr Ser
                340                 345                 350
Ser Ser Ile Trp Gly Pro Thr Cys Asp Gly Leu Asp Arg Ile Val Glu
                355                 360                 365
Arg Cys Asp Leu Pro Glu Met His Val Gly Asp Trp Met Leu Phe Glu
        370                 375                 380
Asn Met Gly Ala Tyr Thr Val Ala Ala Ala Ser Thr Phe Asn Gly Phe
385                 390                 395                 400
Gln Arg Pro Thr Ile Tyr Tyr Val Met Ser Gly Pro Ala Trp Gln Leu
                405                 410                 415
Met Gln Gln Phe Gln Asn Pro Asp Phe Pro Pro Glu Val Glu Glu Gln
                420                 425                 430
Asp Ala Ser Thr Leu Pro Val Ser Cys Ala Trp Glu Ser Gly Met Lys
        435                 440                 445
Arg His Arg Ala Ala Cys Ala Ser Ala Ser Ile Asn Val
450                 455                 460
```

METHODS AND COMPOSITIONS TO PREVENT AND TREAT DISORDERS ASSOCIATED WITH MUTATIONS IN THE ODC1 GENE

CROSS-REFERENCE TO RELATED APPLICATIONS

This application claims the benefit of U.S. Provisional Application No. 62/726,754 filed on Sep. 4, 2018; the entire contents of said application are incorporated herein in its entirety by this reference.

SEQUENCE LISTING

The instant application contains a Sequence Listing which has been filed electronically in ASCII format and is hereby incorporated by reference in its entirety. Said ASCII copy, created on Mar. 23, 2020, is named MSS-02601_SL.txt and is 8,321 bytes in size.

BACKGROUND OF THE INVENTION

Pediatric developmental disorders may include child neurobehavioral disorders as well as disorders that lead to physical disabilities in children. Developmental delays can affect a child's physical, cognitive, communication, social, emotional, or behavioral skills. Often, developmental delays affect more than one area of a child's development. Some developmental delays have an identifiable cause. However, for many children, the cause of the delay, or multiple delays, is not clear. Thus, there is a need for not only identifying underlying causes of developmental delay in pediatric populations but also a need for development of novel therapeutic treatments for these patient populations.

SUMMARY OF THE INVENTION

The invention disclosed herein is based, in part, on the novel discovery of a new pediatric developmental disorder, characterized by one or more mutations in the ODC1 gene, increased polyamine levels, and developmental delay in affected patients. In some aspects, provided herein are methods of treating or preventing a disorder associated with a mutation in a gene encoding a peptide (e.g., a gene encoding a mutated protein, such as a mutated ODC protein) in the polyamine pathway in a subject. In some embodiments, the method comprises administering to the subject at least one agent listed in Table 1. The disorder may be a developmental disorder. In some embodiments, the pediatric developmental disorder is Bachmann-Bupp Syndrome (BABS). In some embodiments, provided herein are methods and compositions for treating or preventing a disorder associated with a mutation in a gene encoding a peptide (e.g., a peptide in FIG. 3) in the polyamine pathway in a subject. In some embodiments, the mutation leads to accumulation of a polyamine (e.g., putrescine).

In some embodiments, the disorder is Snyder-Robinson syndrome. In some embodiments, the genetic mutation is in a spermine synthase gene, leading to a decrease in the biosynthesis of spermine.

In some embodiments, the disorder is characterized by accumulation of a polyamine. In some embodiments, the disorder is characterized by mutations in genes encoding peptides in the polyamine pathway. In some embodiments, the disorder characterized by symptoms disclosed herein. In some embodiments, the disorder is a spectrum disorder.

Provided herein are methods of treating or preventing a disorder associated with a mutation in the ODC1 gene in a subject comprising administering to the subject at least one agent that inhibits the biosynthesis or activity of, or decreases the levels of, an ODC enzyme or a fragment thereof. Also provided herein are methods of treating or preventing a disorder associated with a mutation in the ODC1 gene in a subject comprising administering to the subject at least one agent that inhibits the biosynthesis or activity of, or decreases the levels of, a polyamine.

Also provided herein are methods of treating or preventing a disorder associated with a mutation in the AMD1 gene in a subject comprising administering to the subject at least one agent that increases the biosynthesis or activity of, or increases the levels of, an AMD protein or a fragment thereof. Also provided herein are methods of treating or preventing a disorder associated with a mutation in the AMD1 gene in a subject comprising administering to the subject at least one agent that increases the biosynthesis or activity of, or increases the levels of, an dcAdoMet protein or a fragment thereof. The mutation may be a loss of function mutation. The agent may be recombinant AMD or recombinant dcAdoMet.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
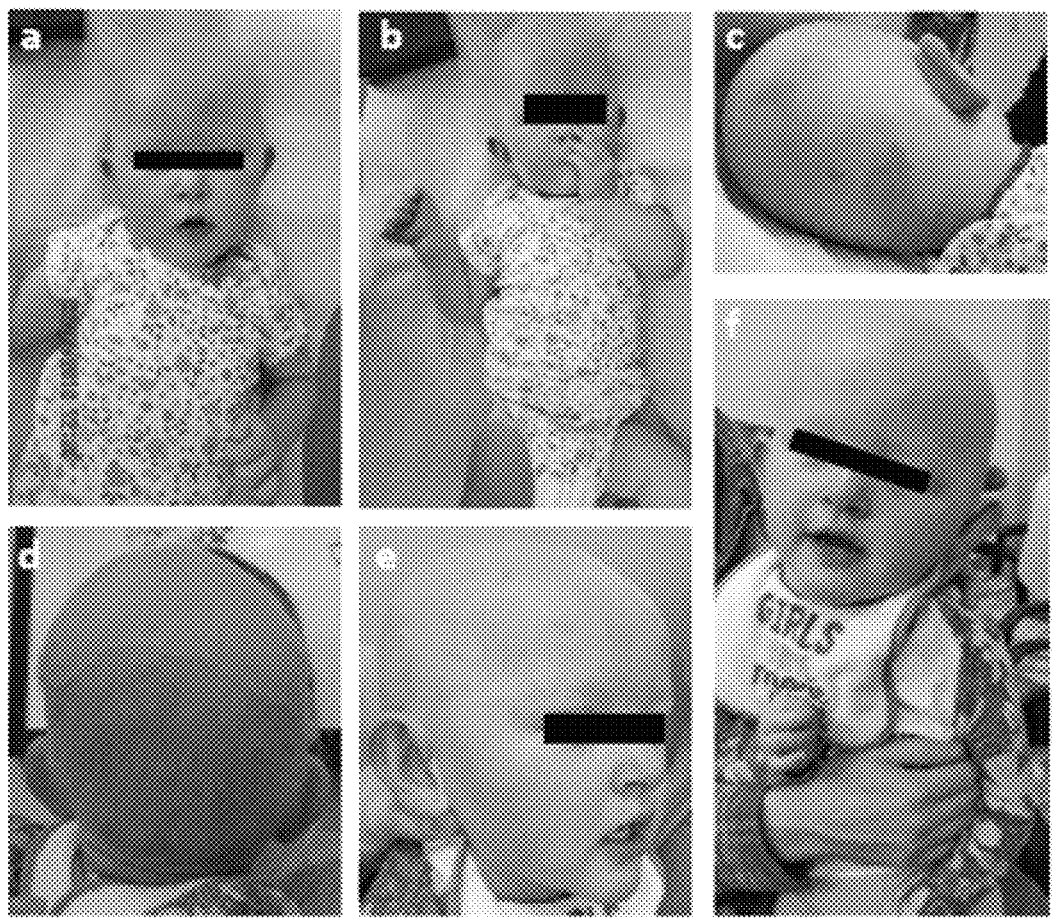
FIG. 1 consists of six parts, Parts A-F, and shows the clinical features of a pediatric patient with a new autosomal dominant syndrome linked to the ODC1 gene. The affected girl is shown at 11 months (Parts A-C) and 32 months of age (Parts D-F) and carries a heterozygous de novo nonsense mutation in ODC1. The main phenotypic features are macrosomia, macrocephaly, developmental delay, alopecia, spasticity, hypotonia, cutaneous vascular malformation, delayed visual maturation, and sensorineural hearing loss (Parts A-F).

In some aspects, provided herein are methods of treating or preventing a disorder associated with a mutation in a gene encoding a peptide in the polyamine pathway in a subject. In some embodiments, the method comprises administering to the subject at least one agent that that inhibits the biosynthesis or activity of, or decreases the levels of, a polyamine (e.g., putrescine, spermidine, spermine). In some embodiments, the method comprises administering to the subject at least one agent listed in Table 1. In some embodiments, the agent is any agent that inhibits the biosynthesis or activity of an ODC enzyme or a fragment thereof. Provided herein are methods of treating or preventing a disorder associated with a mutation in the ODC1 gene in a subject comprising administering to the subject at least one agent that inhibits the biosynthesis or activity of, or decreases the levels of, an ODC enzyme or a fragment thereof. Also provided herein are methods of treating or preventing a disorder associated with a mutation in the ODC1 gene in a subject comprising administering to the subject at least one agent that inhibits the biosynthesis or activity of, or decreases the levels of, a polyamine (e.g., putrescine, spermidine, spermine). In some embodiments, the subject is a human. The subject may be a pediatric subject (e.g., at least under 18 years of age, at least under 10, or at least under 5 years of age). In some embodiments, the agent is DFMO. In some embodiments, the agent is formulated for oral administration.

The ornithine decarboxylase 1 (ODC1) gene plays an important role in physiological and cell developmental processes including embryogenesis, organogenesis, and neoplastic cell growth. Ornithine decarboxylase 1 (ODC1) is a gene and its gene product ODC is a rate-limiting enzyme in the biosynthesis of polyamines (putrescine, spermidine, spermine). ODC converts ornithine (a non proteinogenic amino acid) into putrescine (a diamine).

Here, it is reported that an 11-month old Caucasian female with a heterozygous de novo nonsense mutation in the ODC1 gene that leads to a premature abrogation of 14-aa residues at the ODC protein c-terminus. Phenotypic manifestations include macrosomia, macrocephaly, developmental delay, alopecia, spasticity, hypotonia, cutaneous vascular malformation, delayed visual maturation, and sensorineural hearing loss. A new pediatric disorder that is directly linked to a de novo pathogenic variant in the ODC1 gene is described herein. The ODC1 gene mutation (c.1342 A>T) was identified by whole exome sequencing and confirmed by Sanger sequencing. Red blood cells (RBCs) obtained from the patient showed elevated ODC protein and polyamine levels compared to healthy controls.

Definitions

For convenience, certain terms employed in the specification, examples, and appended claims are collected here.

The articles "a" and "an" are used herein to refer to one or to more than one (i.e., to at least one) of the grammatical object of the article.

As used herein, the term "administering" means providing an agent or composition to a subject, and includes, but is not limited to, administering by a medical professional and self-administering.

The term "agent" is used herein to denote a chemical compound, a small molecule, a mixture of chemical compounds and/or a biological macromolecule (such as a nucleic acid, an antibody, an antibody fragment, a protein or a peptide). The activity of such agents may render them suitable as a "therapeutic agent" which is a biologically, physiologically, or pharmacologically active substance (or substances) that acts locally or systemically in a subject.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

An antibody for use in the instant invention may be a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences.

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the disclosure may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "monoclonal antibody" refers to an antibody obtained from a population of substantially homogeneous antibodies that specifically bind to the same epitope, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the term "subject" means a human or non-human animal selected for treatment or therapy. In certain embodiments, of the methods and compositions described herein the subject is a human subject.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a non-natural arrangement.

The terms "prevent," "preventing," "prevention," and the like refer to reducing the probability of developing a disease, disorder, or condition in a subject, who does not have, but is at risk of or susceptible to developing a disease, disorder, or condition.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

"Treating" a disease in a subject or "treating" a subject having a disease refers to subjecting the subject to a pharmaceutical treatment, e.g., the administration of a drug, such that at least one symptom of the disease is decreased or prevented from worsening.

Methods

In some aspects, provided herein are methods of treating or preventing a disorder associated with a mutation in a gene encoding a peptide in the polyamine pathway in a subject, comprising administering to the subject at least one agent listed in Table 1. Polyamines are ubiquitous small basic molecules that play multiple essential roles in mammalian physiology. As used herein, peptides and molecules that are in the polyamine pathway may refer to any peptide or molecule (e.g., a polycationic small molecule, such as putrescine, spermidine, spermine) that functions in the in eIF5A hypusination and/or polyamine metabolism pathways. Exemplary peptides in this pathway are disclosed herein and can be found in FIG. 3. In some embodiments, the agent decreases the activity of, the biosynthesis of, or decreases the levels of a molecule in FIG. 3 (e.g., putrescine). In some embodiments, the molecule is a polycationic small molecule, such as putrescine, spermidine, spermine. In some embodiments, the disorder is associated with an accumulation of a polycationic small molecule, such as putrescine. In some embodiments, the disorder described herein is associated with a gene mutation that results in an accumulation of a polycationic small molecule. In some embodiments, the disorder is associated with a gain-of-function mutation. In other embodiments, the mutation is associated with a loss-of-function mutation (e.g., a loss-of-function mutation in AMD1, which would lead to an accumulation in putrescine). In some embodiments, the disorder is characterized by mutations in genes encoding a peptide in the polyamine pathway. Examples of such peptides include, but are not limited to, ODC, DHPS, DOHH, AMD1, MAT1A, MAT1B, SRM, SMS, SMOX, MYC, SAT1, PAOX, or EIF5A. MYC may also be referred to as c-MYC, L-MYC, MYCN, and N-MYC.

In some embodiments, the agent is a small molecule. In some embodiments, the agent is an agent that prevents the accumulation of, inhibits the biosynthesis of, or inhibits the activity of a polycationic small molecule, such as putrescine. In some embodiments, the agent is eflornithine (DFMO). Eflornithine, or ornithine decarboxylase inhibitor, or DFMO, or Ornidyl, is an irreversible inhibitor of ornithine decarboxylase (ODC) that inhibits polyamine biosynthesis. In some embodiments, the agent is a DFMO derivative, analog, or prodrug thereof. Exemplary DFMO prodrugs can be found in U.S. patent publication US20100120727, hereby incorporated by reference in its entirety. In some embodiments, the agent is a peptide, such as an antibody. In some embodiments, the agent is an inhibitory polynucleotide.

In some embodiments, the agent inhibits the activity of a peptide and/or enzyme in the polyamine pathway. In some embodiments, the agent inhibits the activity of deoxyhypusine synthase (DHPS). The agent may be GC7. In some embodiments, the agent inhibits to activity of S-adenosyl-methionine decarboxylase (AMD1). Exemplary agents that inhibit the activity of AMD1 include, but are not limited to, SAM486A (CGP48664), CGP40215A, mitoguazone (MGBG), MGBCP, and MDL73811. In some embodiments, the agent inhibits the activity of deoxyhypusine hydroxylase (DOHH). Exemplary agents that inhibit the activity of deoxyhypusine hydroxylase include, but are not limited to, ciclopirox, deferiprone, and mimosine. In some embodiments, the agent activates spermidine/spermine N1-acetyltransferase (SAT1). Examples of such agent include, but are not limited to, BENSPM (i.e., DENSPM, N1,N11-diethyl-norspermine (also known as DE-333 or N1,N11-bis(ethyl) norspermine)), MTD1A, and non-steroidal anti-inflammatory drugs (NSAIDs). The NSAID may be sulindac, aspirin, ketorolac, or celecoxib. In some embodiments, the NSAID is selected from the group consisting of aspirin, aceclofenac, acemethacin, alclofenac, amoxiprin, ampyrone, azapropazone, benorylate, bromfenac, choline and magnesium salicylates, choline salicylate, celecoxib, clofezone, diclofenac potassium, diclofenac sodium, diclofenac sodium with misoprostol, diflunisal, droxicam, lornoxicam, meloxicam, tenoxicam, ethenzamide, etodolac, fenoprofen calcium, faislamine, flurbiprofen, flufenamic acid, ibuprofen, ibuproxam, indoprofen, alminoprofen, carprofen, dexibuprofen, dexketoprofen, fenbufen, flunoxaprofen, indomethacin, ketoprofen, ketorolac, kebuzone, loxoprofen, magnesium salicylate, meclofenamate sodium, metamizole, mofebutazone, oxyphenbutazone, phenazone, sulfinpyrazone, mefenamic acid, meloxicam, methyl salicylate, nabumetone, naproxen, naproxen sodium, nebumetone, oxaprozin, oxametacin, phenylbutazone, proglumetacin, piroxicam, pirprofen, suprofen, rofecoxib, salsalate, salicyl salicylate, salicylamide, sodium salicylate, sulindac, tiaprofenic acid, tolfenamic acid, tolmetin sodium, and valdecoxib. In some embodiments, the agent is a polyamine uptake inhibitor, such as AMXT-1501, Trimer44NMe, ORI 1202, or other polyamine/spermidine analogs such as PG11047/CGC-11047, SL11144/CGC-11144 or DEHSPM.

In some embodiments, the method comprises administering to the subject an additional agent (e.g., two or more, three or more, four or more, or five or more). In some embodiments, the additional agent is an agent listed in Table 1. In some embodiments, the agent is any agent that inhibits the biosynthesis of, or activity of, or the levels of a polyamine. The polyamine may be putrescine. The polyamine may be spermidine or spermine.

In some aspects, provided herein are methods of treating or preventing a disorder in a subject associated with a mutation in the ODC1 gene comprising administering to the subject at least one agent that inhibits the biosynthesis or activity an ODC enzyme or a fragment thereof. In other aspects, provided herein are methods of treating or preventing a disorder associated with a mutation in the ODC1 gene in a subject by administering to the subject at least one agent that inhibits the biosynthesis or activity of, or decreases the levels of (e.g., endogenous levels) a polyamine. Also provided herein are methods of decreasing polyamine levels in a subject with a developmental disorder associated with a mutation in the ODC1 gene by administering to the subject one agent that inhibits the expression of a gene encoding an ODC enzyme or a fragment thereof. The methods described herein also include methods of decreasing polyamine levels in a subject with a developmental disorder associated with a mutation in the ODC1 gene by administering to the subject least one agent that inhibits the biosynthesis of, endogenous levels of, or activity of a polyamine.

In some embodiments, the mutation in the ODC1 gene is a nonsense mutation. The mutation in the ODC1 gene may lead to premature abrogation of at least one (e.g., at least 3, at least 5, at least 10, or at least 15) c-terminal amino acids of the OCD protein. The mutation in the ODC1 gene may lead to premature abrogation of at least 14 c-terminal amino acids of the OCD protein. In some embodiments, the mutation in the ODC1 gene leads to accumulation of a polyamine. The mutation may be c.1342 A>T. In some embodiments, the mutation is p.P427X.

In some aspects, disclosed herein are methods that comprise treating a disorder associated with a mutation in a gene encoding a peptide in the polyamine pathway in a subject. In some embodiments, disclosed herein are methods that comprise treating a disorder associated with a mutation in the OCD1 gene (e.g., a mutation described herein) in a subject. In some embodiments, the disorder is a developmental disorder. The disorder may be characterized by macrosomia, macrocephaly, developmental delay, alopecia, spasticity, hypotonia, cutaneous vascular malformation, delayed visual maturation, and/or sensorineural hearing loss. In some embodiments, the disorder is characterized by at least one (e.g., at least 2, at least 3, at least 4, at least 5) symptom(s) listed in Table 2.

In some embodiments, the agent is a small molecule. In some embodiments, the agent is eflornithine (DFMO). In some embodiments, the agent is a DFMO derivative, analog, or prodrug thereof. In some embodiments, the agent is a peptide, such as an antibody. In some embodiments, the agent is an inhibitory polynucleotide. In some embodiments, the DFMO is dosed such that that ODC activity is not entirely depleted. In some embodiments, the dose is adequate to reduce the levels of ODC protein by at least 5%, at least 10%, at least 15%, at least 20%, at least 25%, at least 30%, at least 35%, at least 40%, at least 45%, at least 50%, at least 55%, at least 60%, at least 65%, at least 70%, or at least 80%. In some embodiments, the method comprises administering to the subject an additional agent (e.g., two or more, three or more, four or more, or five or more) agents. In some embodiments, the additional agent is GC7, SAM486A, AMXT1501, Trimer44Nme, or an NSAID (e.g., an NSAID disclosed herein). In some embodiments, the additional agent is an agent listed in Table 1. In some embodiments, the agent is any agent that inhibits the biosynthesis of, or activity of, or the levels of a polyamine (e.g., a polyamine disclosed herein). In certain embodiments, agents of the invention may be used alone or conjointly administered with additional agent. As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents/bacteria can be administered either in the same formulation or in separate formulations, either concomitantly or sequentially.

TABLE 1

| Target | Modulators (Agents) |
| --- | --- |
| ODC | DFMO (inhibitor) |
| DHPS (DHS) | GC7 (inhibitor) |
| DOHH | ciclopirox, mimosine, deferiprone (inhibitors) |
| AMD1 (SAMDC) | SAM486A (CGP48664), MGBG, MDL 73811 and CGP 40215A, also MGBCP (inhibitors) |
| SAT1 (SSAT) | BENSPM, MTD1A, NSAIDS (sulindac, aspirin, ketorolac, Celebrex, etc.) (activators) |
| Polyamine Uptake Inhibitors | AMXT-1501, Trimer44NMe, ORI 1202, PG11047/CGC-11047, SL11144/CGC-11144, or DEHSPM (inhibitors) |

Mutations in ODC1 can either lead to "loss-of-function" (LOF) or "gain-of-function" (GOF) mutations, depending on the precise location of the mutation within ODC. Loss-of-function may occur if the mutation occurs in an area of the gene that encodes for critical sites required to form a proper homodimer (ODC is only functionally active if two identical monomer chains are joined to form a homodimer). Loss-of-function may also occur if the mutation occurs in the enzymatic active center or at a site that allows the binding of a cofactor (pyridoxal 5-phosphate; PLP). A gain-of-function may occur if the mutation occurs in the 3'-end of the ODC1 gene (which means, the c-terminal end of the ODC protein). The last 37 amino acid residues of the ODC protein have been determined to serve as a "destabilization region". This means, if the destabilization region is present, the protein will be properly cleared from the cell/body, through a mechanism called ubiquitin-independent proteasomal degradation. However, if the destabilization region is deleted (for example, through a mutation that introduces a premature stop codon, as is the case in the BABS patient disclosed in the exemplification) then the protein cannot be degraded and consequently will accumulate in the body-thus leading to higher ODC enzyme activity.

Figure 4:
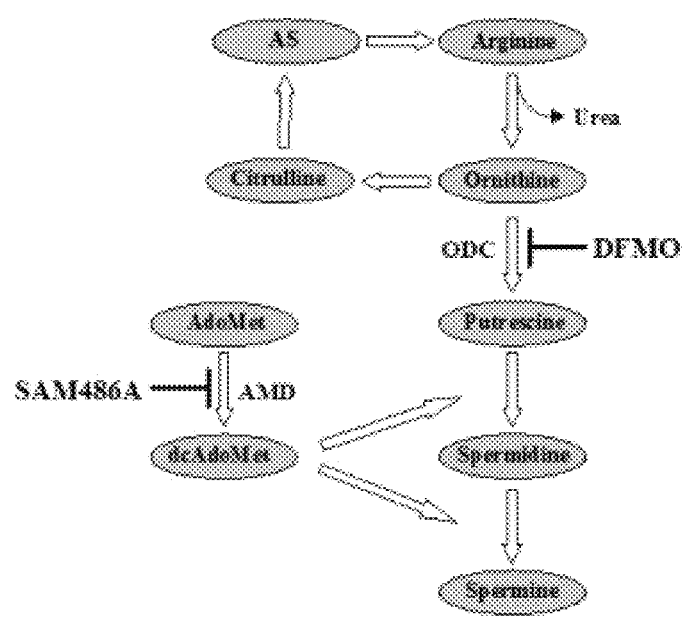
FIG. 4 illustrates the polyamine biosynthetic pathway.

The polyamine biosynthetic pathway is depicted in FIG. 4.

Gain-of-function may also occur if the mutation occurs not in the c-terminal tail but in a region of ODC1 that is needed to properly bind a protein called antizyme (AZ). There are three antizymes known, AZ1, AZ2, and AZ3. AZ is an ODC-interacting protein that triggers the (ubiquitin-independent) degradation of ODC. Binding of AZ to ODC induces a conformational change in the ODC c-terminus which induces degradation in the proteasome (and that is why the tail is so important for degradation—if the c-terminal ODC tail is missing the AZ binding will not lead to this c-terminal conformation change and will not degrade the protein. A mutation in AZ could destroy the interaction site with ODC and without AZ properly binding to ODC, the degradation will also not be triggered.

Not all ODC mutations in the 37-aa region will lead to gain-of-function mutations. In some embodiments, the gain-of-function mutation effectively leads to premature abrogation of protein synthesis through a stop codon, somewhere within the 37-aa destabilization region of the c-terminus. Some mutations may be "silent" and might not have an effect. Other mutations may exchange one amino acid with another (similar) amino acid, and will leave the protein intact and degradable. However, some mutations may prevent ODC degradation differently; not through a stop codon but by modifying the tertiary structure in such a dramatic way (for example, if a mutation leads to the introduction of the amino acid proline, which introduces a "nick" in the tertiary structure of the protein). Such mutations could also lead to gain-of-function.

In some embodiments, patients with a gain-of-function mutation in ODC1, and not patients with a loss-of-function mutation, would be considered BABS patients (i.e., an exemplary developmental disorder disclosed herein characterized by with higher ODC levels and putrescine levels).

Therefore, in some embodiments, the disorders described herein result from a gain-of-function mutation. In some aspects, provided herein are methods of determining whether a subject (e.g., a pediatric subject) suffers from a developmental disorder described herein. In some aspects, the methods provided herein include treating a developmental disorder in a subject by administering to the subject an agent that inhibits the activity of or decreases the levels of ODC.

A test for newborns would be beneficial to identify the potential risks, as early as possible, at a time when therapeutic intervention might still be a more effective option. A blood sample (or possible a dry blot spot) could be used to test for mutations in the ODC gene. In addition, the test could comprise determining the ODC protein blood levels as well as the blood levels of polyamines putrescine, spermidine, and spermine (or acetylated variations thereof). ODC enzymatic activity could be tested in the blood. Urine could also be tested for polyamine levels (or acetylated variations thereof) and used as a noninvasive approach and biomarker. For example, patients with a gain-of-function mutation would show higher ODC protein levels, which means higher ODC enzyme activity levels and also higher putrescine and possibly spermidine levels. In some embodiments, the developmental disorder is characterized by an increase in ODC activity or ODC levels (e.g., at least a 10%, at least 20%, at least 30%, at least a 40%, at least 50%, at least 60%, at least a 70%, at least 80%, or at least 90% increase in ODC activity or ODC levels). An increase in levels or activity of ODC may be measured by comparing the levels of or activity of ODC in the subject to the levels of or activity of ODC in pediatric or adult subject (or group of subjects, such as an average from a group of subjects) not afflicted with a developmental disorder disclosed herein.

In some aspects, provided herein are methods of determining whether a subject is afflicted with a developmental disorder (e.g., a developmental disorder disclosed herein), the method comprising obtaining a biological sample from the subject, sequencing at least a portion of the subject's genome comprising the ODC1 gene, determining if the subject has a gain-of-function mutation in OCD1 gene, and, if the subject has a gain-of-function mutation in the OCD1 gene, the subject has the developmental disorder. In some aspects, provided herein are methods of treating a developmental disorder in a subject, the method comprising obtaining a biological sample from the subject, sequencing at least a portion of the subject's genome comprising the OCD1 gene, determining whether the subject has a gain-of-function mutation in the OCD1 gene, and, if the subject has a gain-of-function mutation in the OCD1 gene, administering to the subject an agent that inhibits of the activity of or the levels of ODC. The mutation may result in increased levels of or activity of OCD. In some embodiments, the mutation leads to premature abrogation of protein synthesis through a stop codon within the 37-aa destabilization region of the c-terminus. In some embodiments, the mutation is a mutation in the antizyme binding portion of ODC. The mutations in ODC1 described herein may result in accumulation of ODC. The mutation my result in decrease in the degradation of ODC. In some embodiments, the mutation leads to a modification of the tertiary structure of the protein. In some embodiments, the mutations lead the introduction of the amino acid proline, which introduces a "nick" in the tertiary structure of the protein.

In some aspects, provided herein are methods of determining whether a subject is afflicted with a developmental disorder (e.g., a developmental disorder disclosed herein), the method comprising obtaining a biological sample from the subject, sequencing at least a portion of the subject's genome comprising the ODC1 gene, determining if the subject has a mutation in the c-terminal 37 amino acids in the OCD1 gene, and, if the subject has a mutation in the c-terminal 37 amino acids in the OCD1 gene, the subject has the developmental disorder. In some aspects, provided herein are methods of treating a developmental disorder in a subject, the method comprising obtaining a biological sample from the subject, sequencing at least a portion of the subject's genome comprising the ODC1 gene, determining whether the subject has a mutation in the c-terminal 37 amino acids in the OCD1 gene, and, if the subject has a mutation in the c-terminal 37 amino acids in the OCD1 gene, administering to the subject an agent that inhibits of the activity of or the levels of ODC. The mutation may be a gain-of-function mutation. The mutation may result in increased levels of or activity of OCD. In some embodiments, the mutation leads to premature abrogation of protein synthesis through a stop codon, somewhere within the 37-aa destabilization region of the c-terminus. The mutations in ODC1 described herein may result in accumulation of ODC. The mutation my result in decrease in the degradation of ODC.

In some aspects, provided herein are methods of determining whether a subject is afflicted with a developmental disorder (e.g., a developmental disorder disclosed herein), the method comprising obtaining a biological sample from the subject, sequencing at least a portion of the subject's genome comprising the ODC1 gene, determining if the subject has a mutation in the antizyme (AZ) binding portion of the OCD1 gene, and, if the subject has a mutation in the antizyme (AZ) binding portion of the OCD1 gene, the subject has the developmental disorder. In some aspects, provided herein are methods of treating a developmental disorder in a subject, the method comprising obtaining a biological sample from the subject, sequencing at least a portion of the subject's genome comprising the ODC1 gene, determining whether the subject has a mutation in the antizyme (AZ) binding portion of the OCD1 gene, and, if the subject has a mutation in in the antizyme (AZ) binding portion of the OCD1 gene, administering to the subject an agent that inhibits of the activity of or the levels of ODC. The mutation may be a gain-of function mutation. The mutation may result in accumulation of ODC. The mutation my result in decrease in the degradation of ODC.

In some aspects, provided herein are methods of determining whether a subject is afflicted with a developmental disorder (e.g., a developmental disorder disclosed herein), the method comprising obtaining a biological sample from the subject, measuring ODC enzyme activity or ODC levels in the biological sample, and, if the subject has increased ODC enzyme activity or ODC levels, the subject has the developmental disorder. In some aspects, provided herein are methods of treating a developmental disorder (e.g., a developmental disorder disclosed herein) in a subject, the method comprising obtaining a biological sample from the subject, measuring ODC enzyme activity and/or levels of ODC in the biological sample, and, if the subject has increased ODC enzyme activity and/or levels of ODC, administering to the subject an agent that inhibits of the activity of or the levels of ODC.

In some aspects, provided herein are methods of determining whether a subject is afflicted with a developmental disorder (e.g., a developmental disorder disclosed herein), the method comprising obtaining a biological sample from the subject, measuring the levels of polyamine or acetylated variations thereof in the biological sample, and, if the subject has increased polyamine levels or acetylated variations thereof, the subject has the developmental disorder.

In some embodiments, an increase in ODC enzyme activity or an increase in ODC levels is measured by comparing the biological sample to a control sample (i.e., a sample from a subject who is not afflicted with a developmental disorder disclosed herein). In some embodiments, an increase in ODC enzyme activity or ODC levels is measured by comparing the biological sample to a range and/or average of ODC enzyme activity or ODC levels from a population of subjects not afflicted with a developmental disorder disclosed herein. In some embodiments, administration of an agent leads to a decrease in the levels of or activity of ODC (e.g., at least a 10%, at least a 20%, at least a 30%, at least a 40%, at least a 50%, at least a 60%, at least a 70%, at least a 80%, or at least a 90% decrease) in ODC levels or activity.

S-adenosylmethionine decarboxylase (AMD1) is a gene and its gene product AMD is the second rate-limiting enzyme in the biosynthesis of polyamines. SAM486A inhibits the enzymatic activity of AMD (also known as SAMDC or AdoMetDC). AMD is necessary to convert AdoMet into decarboxylated AdoMet (dcAdoMet). dcAdoMet is a required substrate for the conversion of putrescine to spermidine, by the action of spermidine synthase. If the AMD1 gene is mutated such that it becomes deficient (loss-of-function; LOF), the enzyme is inactive. This means no dcAdoMet is synthesized. Without dcAdoMet, putrescine cannot be further converted to spermidine. This creates a "putrescine back-log" and leads to putrescine accumulation. Blocking the enzyme (essentially mimicking the LOF in AMD1) may lead to putrescine accumulation in cells. Therefore, in some embodiments, a subject described herein (i.e., a subject with a developmental disorder disclosed herein) may have a loss-of-function mutation in AMD1. The loss-of-function mutation may lead to an accumulation of putrescine. In some embodiments, a developmental disorder disclosed herein is associated with a loss-of-function mutation in AMD1. In some aspects, the developmental disorder is characterized by a decrease in the levels of or activity of AMD (e.g., at least a 10%, at least a 20%, at least a 30%, at least a 40%, at least a 50%, at least a 60%, at least a 70%, at least a 80%, or at least a 90% decrease) in AMD levels or activity. A decrease in AMD levels or activity may be measured by comparing the level of or activity of AMD of a subject who is afflicted with a developmental disorder disclosed herein to the level of or activity of AMD in pediatric or adult subjects not afflicted with a developmental disorder disclosed herein. In some embodiments, a decrease in AMD enzyme activity or levels is measured by comparing the AMD levels or activity in the biological sample of an afflicted subject to a range and/or average of AMD enzyme activity or AMD levels from a population of subjects not afflicted with a developmental disorder disclosed herein.

In some embodiments, the developmental disorder is characterized by a decrease in the levels of or activity of dcAdoMet (e.g., at least a 10%, at least a 20%, at least a 30%, at least a 40%, at least a 50%, at least a 60%, at least a 70%, at least a 80%, or at least a 90% decrease) in dcAdoMet levels or activity. A decrease in levels or activity of dcAdoMet may be measured by comparing the levels of or activity of dcAdoMet in the afflicted subject to the levels of or activity of dcAdoMet in pediatric or adult subjects not afflicted with a developmental disorder disclosed herein.

In some embodiments, the developmental disorder is characterized by a decrease in the levels of or activity of AdoMet (e.g., at least a 10%, at least a 20%, at least a 30%, at least a 40%, at least a 50%, at least a 60%, at least a 70%, at least a 80%, or at least a 90% decrease) in AdoMet levels or activity. A decrease in levels or activity of AdoMet may be measured by comparing the levels of or activity of AdoMet in the afflicted subject to the levels of or activity of AdoMet in pediatric or adult subjects not afflicted with a developmental disorder disclosed herein.

In some aspects, provided herein are methods of determining whether a subject is afflicted with a developmental disorder, the method comprising, obtaining a biological sample from the subject, sequencing at least a portion of the subject's genome comprising the AMD1 gene, determining whether the subject has a loss-of-function mutation in the AMD1 gene, and, if the subject has loss-of-function mutation in the AMD1 gene, the subject is afflicted with the developmental disorder. The mutation may result in decreased AMD levels or AMD activity. In some embodiments, the mutation results in an increase in polyamine levels.

In some aspects, provided herein are methods of determining whether a subject is afflicted with a developmental disorder, the method comprising obtaining a biological sample from the subject, measuring AMD enzyme activity or levels of A in the biological sample, and, if the subject has decreased AMD enzyme activity, the subject is afflicted with the developmental disorder. In some aspects, provided herein are methods of treating a developmental disorder in a subject, the method comprising, obtaining a biological sample in a subject, sequencing at least a portion of the subject's genome comprising the AMD1 gene, determining whether the subject has loss-of-function mutation in the AMD1 gene, and, if the subject has a loss-of-function mutation in the AMD1 gene, administering to the subject an agent that increases of the activity of or the levels of AMD. Also provided herein are methods of treating a developmental disorder in a subject by obtaining a biological sample from the subject, measuring AMD enzyme activity or levels of AMD in the biological sample, and, if the subject has decreased AMD enzyme activity or levels of AMD, administering to the subject an agent that increases of the activity of or the levels of AMD.

A method of determining whether a subject is afflicted with a developmental disorder (e.g., a developmental disorder disclosed herein), the method comprising obtaining a biological sample from the subject, measuring the levels of or activity of dcAdoMet in the biological sample, and, if the subject has decreased levels of or activity of dcAdoMet, the subject is afflicted with the developmental disorder.

A method of treating a developmental disorder (e.g., a developmental disorder disclosed herein), the method comprising obtaining a biological sample from the subject, measuring the levels of or activity of dcAdoMet in the biological sample, and, if the subject has decreased levels of or activity of dcAdoMet, administering to the subject an agent that increases the activity of or the levels of dcAdoMet.

In some embodiments, the agent is a recombinant AMD or recombinant dcAdoMet (i.e., encoded by the recombinant polynucleotides, such as recombinant polynucleotides disclosed herein).

In some aspects, provided herein are methods of treating a developmental disorder (e.g., a developmental disorder disclosed herein), the method comprising obtaining a biological sample from the subject, and measuring the levels of polyamine or acetylated variations thereof in the biological sample. In some embodiments, if the subject has increased levels of polyamine acetylated variations thereof, the method further comprises administering to the subject an agent that inhibits the activity of or the levels of ODC (e.g., DFMO). In other embodiments, if the subject has increased polyamine levels, the method further comprises administering to the subject an agent that increases or enhances of the activity of or the levels of AMD.

As described herein, methods of measuring the levels of polyamines or acetylated variations thereof, sequencing at least a portion of the subject's genome, or measuring the activity of or levels of ODC or AMD may be done in combination or sequentially, e.g., methods described herein may include obtaining a biological sample from the subject, sequencing at least a portion of the subject's genome, and analyzing enzymatic activity or levels, and/or measuring the polyamine levels in the biological sample.

In some embodiments, a biological sample is obtained from the subject. The biological sample may be any biological sample in which the subject's DNA can be sequenced and/or the subject's endogenous polyamine levels may be measured. For example, the biological sample may be a biological sample which comprises blood or urine. To sequence gene mutations, any sequencing method known in the art may be used. For example, the methods described herein may include obtaining a biological sample from the subject and isolating the subject's DNA. DNA sequencing by any known technique in the art, including, but not limited to, Maxam Gilbert sequencing, Sanger sequencing, shotgun sequencing, bridge PCR, or next generation sequencing methods, such as massively parallel signature sequencing (MPSS), polony sequencing, 454 pyrosequencing, Illumina (Solexa) sequencing, SOLiD sequencing, Ion torrent semiconductor sequencing, DNA nanoball sequencing, heliscope single molecule sequencing, single molecule real time (SMRT) sequencing, or nanopore DNA sequencing.

Measuring ODC protein may comprise contacting the biological sample with an antibody or antigen binding fragment thereof specific for ODC and analyzing binding with SDS-page or western blot. Measuring AMD protein or dcAdoMet protein may comprise contacting the biological sample with an antibody or antigen binding fragment thereof specific for AMD or dcAdoMet, respectively, and analyzing binding via, for example, SDS-page or western blot. In some embodiments, ODC enzyme activity can be measured by running a radioactive 14-C ornithine assay. Radioactive assays to detect ODC can be found in Hyvönen, M. T., Keinänen, T. and Alhonen, L. (2014). *Assay of Ornithine Decarboxylase and Spermidine/Spermine N1-acetyltransferase Activities*. Bio-protocol 4(22): e1301, hereby incorporated by reference in its entirety. Levels of AdoMet and dcAdoMet in a biological sample may be measured by any technique known in the art, including, but not limited to, high performance liquid phase chromatography (HPLC). Chromatography is a separation process involving two phases, one stationary and the other mobile. Typically, the stationary phase is a porous solid (e.g., glass, silica, or alumina) that is packed into an open-tube capillary, while the mobile phase flows through the packed bed or column.

Any method to measure the levels/titers of polyamines (putrescine, spermidine, spermine) and acetylated polyamine variants in biological samples may be used. For example, a reverse-phase HPLC method may be used to measure polyamine levels. Alternatively, polyamines in biological samples may be detected by mass spectrometry analysis. Mass spectrometers operate by converting the analyte molecules to a charged (ionised) state, with subsequent analysis of the ions and any fragment ions that are produced during the ionization process, on the basis of their mass to charge ratio (m/z). Several different technologies are available for both ionization and ion analysis, resulting in many different types of mass spectrometers with different combinations of these two processes. Examples of ionization processes include, but are not limited to, electrospray ionization (ESI), atmospheric pressure chemical ionization (APCI), and atmospheric pressure photo-ionization (APPI).

Compositions

In some aspects, disclosed herein are compositions to prevent and treat a developmental disorder (e.g., a pediatric developmental disorder) described herein.

Small Molecule Agents

Figure 3:
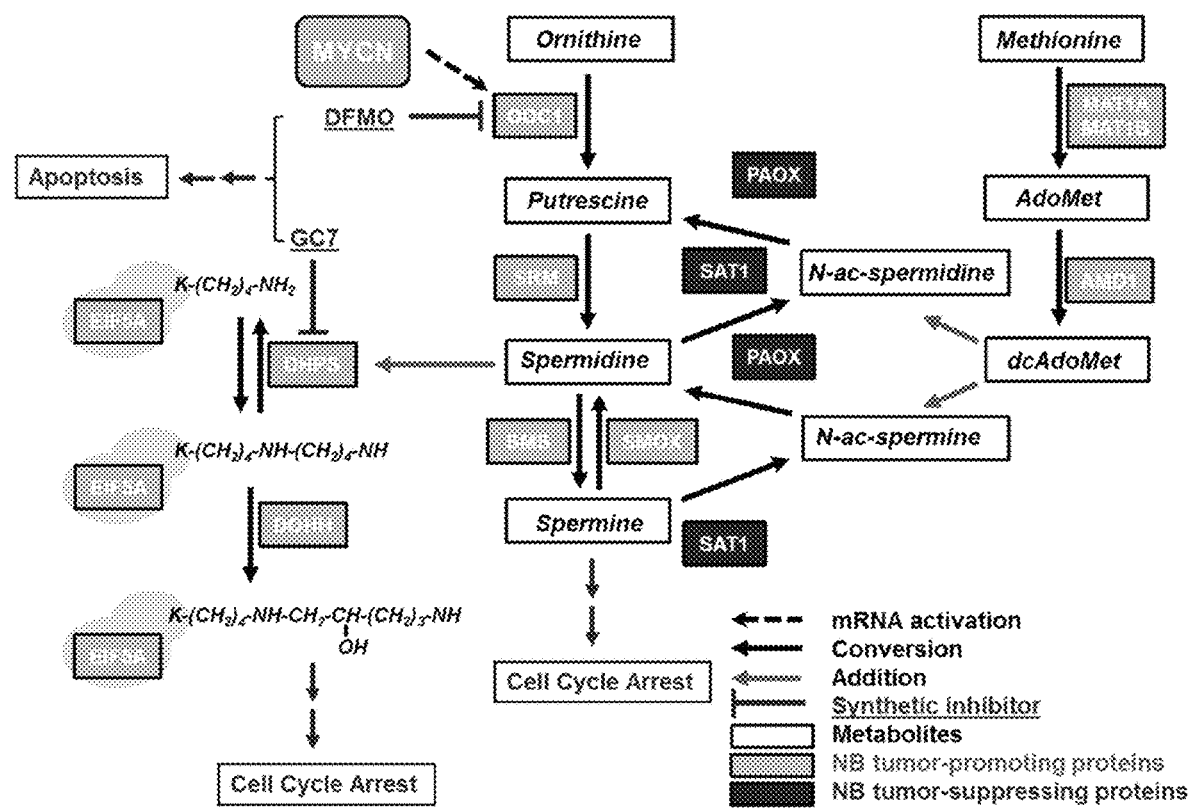
FIG. 3 shows a graphical over view of genes involved in the polyamine pathway.

Certain embodiments of the methods and compositions disclosed herein relate to the use of small molecule agents e.g., small molecule agents that inhibit the activity of a protein or peptide in FIG. 3, for inhibiting the activity or decreasing or increasing the levels of a polyamine (e.g., a polyamine disclosed herein), in a subject. Such agents include those known in the art and those identified using the screening assays described herein. A small molecule provided herein may have at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100% specificity for a peptide in FIG. 3.

In some embodiments, assays used to identify agents in the methods described herein include obtaining a population of cells and a small molecule agent, wherein the cells are incubated with a small molecule agent and the increase or decrease of a polyamine is subsequently measured. Agents identified via such assays, may be useful, for example, for modulating the polyamine pathway in a subject.

Agents useful in the methods disclosed herein may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Antibody Agents

In some embodiments, the agent described herein is an antibody specific for a peptide in the polyamine pathway. An antibody disclosed herein may inhibit expression or activity of a peptide in the polyamine pathway (e.g., a peptide in FIG. 3) by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%. An antibody provided herein may have at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100% specificity for a peptide in FIG. 3.

Antibodies may be polyclonal or monoclonal; xenogeneic, allogeneic, or syngeneic; or modified forms thereof (e.g. humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

In certain embodiments, the methods and compositions provided herein relate to antibodies and antigen binding fragments thereof that bind specifically to a peptide in the polyamine pathway. In some embodiments, the antibodies inhibit the function of the protein, such as inhibiting the activity of the protein, or interfering with protein-protein interactions. Such antibodies can be polyclonal or monoclonal and can be, for example, murine, chimeric, humanized or fully human. In some embodiments, the agent may be a recombinant antibodies, such as chimeric or humanized monoclonal antibodies, can be made using standard recombinant DNA techniques. Such chimeric and humanized monoclonal antibodies can be produced by recombinant DNA techniques known in the art, for example using methods described in U.S. Pat. Nos. 4,816,567; 5,565,332; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Human monoclonal antibodies specific for a peptide in the polyamine pathway can be generated using transgenic or transchromosomal mice carrying parts of the human immune system rather than the mouse system. For example, "HuMAb mice" which contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, N. et al. (1994) *Nature* 368(6474): 856 859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N.Y Acad. Sci 764:536 546). The preparation of HuMAb mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807.

Polypeptide Agents

In some embodiments, the agent provided herein is a polypeptide agent (e.g., a polypeptide that binds to a protein in the polyamine pathway). A polypeptide agent disclosed herein may inhibit the expression or activity of a peptide in the polyamine pathway (e.g., a peptide in FIG. 3) by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%. A polypeptide agent disclosed herein may inhibit the binding of a peptide in the polyamine pathway to another protein by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%. In some embodiments, the agent may be a chimeric or fusion polypeptide. A fusion or chimeric polypeptide can be produced by standard recombinant DNA techniques. For example, DNA fragments coding for the different polypeptide sequences are ligated together inframe in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Ausubel et al., eds., John Wiley & Sons: 1992). Moreover, many expression vectors are commercially available that already encode a fusion moiety.

The polypeptides described herein can be produced in prokaryotic or eukaryotic host cells by expression of polynucleotides encoding a polypeptide(s). Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference.

Nucleic Acid Agents

In certain embodiments, interfering nucleic acid molecules that selectively target and inhibit the activity or expression of a product (e.g., an mRNA product) of a gene encoding a peptide in the polyamine pathway (e.g., a peptide in FIG. 3) are provided herein and/or used in methods described herein. An agent may inhibit the expression or activity of a product (e.g., an mRNA product) of a gene encoding a peptide in the polyamine pathway (e.g., a peptide in FIG. 3) by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%. An agent disclosed herein may comprise at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100% complementarity to a product (e.g., an mRNA product) of a gene encoding a protein in FIG. 3.

In some embodiments, the inhibiting nucleic acid is a siRNA, a shRNA, a PNA, or a miRNA molecule. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, single-stranded siRNA molecules, miRNA molecules and shRNA molecules.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acid molecule is double-stranded RNA. The double-stranded RNA molecule may have a 2 nucleotide 3' overhang. In some embodiments, the two RNA strands are connected via a hairpin structure, forming a shRNA molecule. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

Interfering nucleic acid molecules provided herein can contain RNA bases, non-RNA bases or a mixture of RNA bases and non-RNA bases. For example, interfering nucleic acid molecules provided herein can be primarily composed of RNA bases but also contain DNA bases or non-naturally occurring nucleotides.

The interfering nucleic acids can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, incorporated by reference in their entireties.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications. The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

"Phosphorothioates" (or S-oligos) are a variant of normal DNA in which one of the nonbridging oxygens is replaced by a sulfur. The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990). The latter methods avoid the problem of elemental sulfur's insolubility in most organic solvents and the toxicity of carbon disulfide. The TETD and BDTD methods also yield higher purity phosphorothioates.

"2'O-Me oligonucleotides" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligonucleotides (PTOs) for further stabilization. 2'O-Me oligonucleotides (phosphodiester or phosphothioate) can be synthesized according to routine techniques in the art (see, e.g., Yoo et al., Nucleic Acids Res. 32:2008-16, 2004).

The interfering nucleic acids described herein may be contacted with a cell or administered to an organism (e.g., a human). Alternatively, constructs and/or vectors encoding the interfering RNA molecules may be contacted with or introduced into a cell or organism. In certain embodiments, a viral, retroviral or lentiviral vector is used. In some embodiments, the vector has a tropism for cardiac tissue. In some embodiments the vector is an adeno-associated virus.

In some embodiments, the interfering nucleic acid molecule is a siRNA molecule. Such siRNA molecules should include a region of sufficient homology to the target region, and be of sufficient length in terms of nucleotides, such that the siRNA molecule down-regulate target RNA. The term "ribonucleotide" or "nucleotide" can, in the case of a modified RNA or nucleotide surrogate, also refer to a modified nucleotide, or surrogate replacement moiety at one or more positions. It is not necessary that there be perfect complementarity between the siRNA molecule and the target, but the correspondence must be sufficient to enable the siRNA molecule to direct sequence-specific silencing, such as by RNAi cleavage of the target RNA. In some embodiments, the sense strand need only be sufficiently complementary with the antisense strand to maintain the overall double-strand character of the molecule.

In addition, an siRNA molecule may be modified or include nucleoside surrogates. Single stranded regions of an siRNA molecule may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA molecule, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

A "small hairpin RNA" or "short hairpin RNA" or "shRNA" includes a short RNA sequence that makes a tight hairpin turn that can be used to silence gene expression via RNA interference. The shRNAs provided herein may be chemically synthesized or transcribed from a transcriptional cassette in a DNA plasmid. The shRNA hairpin structure is cleaved by the cellular machinery into siRNA, which is then bound to the RNA-induced silencing complex (RISC).

Non-limiting examples of shRNAs include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In some embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional embodiments related to the shRNAs, as well as methods of designing and synthesizing such shRNAs, are described in U.S. patent application publication number 2011/0071208, the disclosure of which is herein incorporated by reference in its entirety for all purposes.

In some embodiments, provided herein are micro RNAs (miRNAs). miRNAs represent a large group of small RNAs produced naturally in organisms, some of which regulate the expression of target genes. miRNAs are formed from an approximately 70 nucleotide single-stranded hairpin precursor transcript by Dicer. miRNAs are not translated into proteins, but instead bind to specific messenger RNAs, thereby blocking translation. In some instances, miRNAs base-pair imprecisely with their targets to inhibit translation.

In certain embodiments, antisense oligonucleotides may be 100% complementary to the target sequence, or may include mismatches, e.g., to improve selective targeting of allele containing the disease-associated mutation, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability.

Interfering nucleic acid molecules can be prepared, for example, by chemical synthesis, in vitro transcription, or digestion of long dsRNA by Rnase III or Dicer. These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

In the present methods, an interfering nucleic acid molecule or an interfering nucleic acid encoding polynucleotide can be administered to the subject, for example, as naked nucleic acid, in combination with a delivery reagent, and/or as a nucleic acid comprising sequences that express an interfering nucleic acid molecule. In some embodiment, the interfering nucleic acid is administered directly to a tumor in a subject. In some embodiments, the nucleic acid comprising sequences that express the interfering nucleic acid molecules are delivered within vectors, e.g. plasmid, viral and bacterial vectors. Any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Res., 32(13): e109 (2004); Hanai et al. Ann NY Acad Sci., 1082:9-17 (2006); and Kawata et al. Mol Cancer Ther., 7(9):2904-12 (2008); each of which is incorporated herein in their entirety. Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference in its entirety.

In some embodiments of the methods described herein, liposomes are used to deliver an inhibitory oligonucleotide to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019, 369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

In some embodiments, the agent disclosed herein is an agent for genome editing (e.g., an agent used to repair a nucleotide base pair(s) which encode a mutated protein to a nucleotide base pair(s) which encode the non-mutated protein). The agent may repair any genetic mutation that leads to the accumulation of a polyamine disclosed herein. Deletion and repair of DNA may be performed using gene therapy to disrupt the target gene. In some embodiments, the agent comprises a CRISPR-Cas9 guided nuclease and/or a sgRNA (Wiedenheft et al., "RNA-Guided Genetic Silencing Systems in Bacteria and Archaea," *Nature* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7):397-405 (2013), which are hereby incorporated by reference in their entirety). CRISPR-Cas9 interference is a genetic technique which allows for sequence-specific control of gene expression in prokaryotic and eukaryotic cells by guided nuclease double-stranded DNA cleavage. It is based on the bacterial immune system-derived CRISPR (clustered regularly interspaced palindromic repeats) pathway. In some embodiments, the agent is an sgRNA. An sgRNA combines tracrRNA and crRNA, which are separate molecules in the native CRISPR/Cas9 system, into a single RNA construct, simplifying the components needed to use CRISPR/Cas9 for genome editing. In some embodiments, a portion of the crRNA of the sgRNA has complementarity to at least a portion of a gene that encodes a protein in FIG. 3. In some embodiments, the sgRNA may target at least a portion of a gene which encodes a protein in FIG. 3 (e.g., OCD or AMD). In some embodiments, CRISPR technology is used to replace a fragment(s) of the genome that is mutated. In some embodiments, CRISPR technology is used to knock-in and/ or replace portions of the genome that comprise loss-of-function mutations (e.g., loss-of-function mutations in AMD1).

In some embodiments, the agent is a nuclease (e.g., a zinc finger nuclease or a TALEN). Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. Other technologies for genome customization that can be used to knock out genes are meganucleases and TAL effector nucleases (TALENs). A TALEN is composed of a TALE DNA binding domain for sequence-specific recognition fused to the catalytic domain of an endonuclease that introduces double-strand breaks (DSB). The DNA binding domain of a TALEN is capable of targeting with high precision a large recognition site (for instance, 17 bp). Meganucleases are sequence-specific endonucleases, naturally occurring "DNA scissors," originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes).

In some embodiments, the methods described herein is an agent that activates or increases the levels of a peptide in the polyamine pathway. In some embodiments, the agent is an mRNA molecule and/or a vector encoding an mRNA molecule. In certain embodiments, the methods provided herein relate to agents that enhance the expression and/or activity of SAT1. For example, the agent may be an mRNA that encodes for a SAT1 peptide. In some embodiments, the nucleic acid is linked to a promoter and/or other regulatory sequences. In some embodiments, the nucleic acid comprises a sequence that is at least about 80%, 85%, 90%, 95%, 98%, 99% or 100% identical to a nucleotide sequence provided herein.

In certain embodiments, provided herein is a composition, e.g., a pharmaceutical composition, containing at least one agent described herein together with a pharmaceutically acceptable carrier. In one embodiment, the composition includes a combination of multiple (e.g., two or more) agents described herein.

As described in detail below, the pharmaceutical compositions disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous, intrathecal, intracerebral or epidural injection as, for example, a sterile solution or suspension, or sustained-release formulation.

Methods of preparing these formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, dimethyl sulfoxide (DMSO), polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents provided herein, which may be used in a suitable hydrated form, and/or the pharmaceutical compositions disclosed herein, are formulated into pharmaceutically-acceptable dosage forms by conventional methods known to those of skill in the art.

As can be appreciated from the disclosure above, the present invention has a wide variety of applications. The invention is further illustrated by the following examples, which are only illustrative and are not intended to limit the definition and scope of the invention in any way.

Exemplification

Study Participants and Consent

The female Caucasian patient was examined at Helen DeVos Children's Hospital (Grand Rapids, Mich., USA) first at 11 months of age. Whole blood samples for testing were drawn at age 19 months (whole-exome sequencing) and 32 months (ODC protein and PA). Two developmentally normal, age/gender matched patients that were being sedated for outpatient same-day procedures served as controls. The parents of the patients provided written informed consent. The protocol was approved by the institutional review board (IRB) of Spectrum Health.

Whole-Exome Sequencing

Since a clear diagnosis could not be made for this patient, whole-exome sequencing (WES) was ordered. Freshly drawn blood was shipped to GeneDx (Gaithersburg, Md., USA) for analysis. After DNA extraction using genomic DNA, the Agilent Clinical Research Exome kit was used to target exonic regions and flanking splice junctions of the genome. These were sequenced on Illumina HiSeq with 100 bp paired-end reads. Bi-directional sequence was assembled and aligned based on GRCh37/USC hg19 for analysis using their custom-developed analysis tool. Sanger sequencing was performed to confirm the ODC1 variant which was classified as a candidate gene with potential relationship to disease phenotype but a variant of uncertain significance. Parental samples were also sent for exome testing and neither maternal nor paternal sample showed the ODC1 variant.

Blood Collection and Processing

Freshly drawn blood from the patient was collected in the clinic and sent for WES as stated above. A separate collection of blood (5 mL) from the patient and two controls were ordered. Whole blood was collected in K2/EDTA tubes and spun immediately at 400 g for 15 min at 4° C. The supernatant plasma was removed, and spun at 10,000 g for 10 min to remove cell debris. The buffy coat layer was removed from the pelleted red blood cells (RBCs). RBCs and plasma were stored at −80° C. prior to protein or polyamine isolation and detection. In some embodiments, the blood from a patient may be analyzed through whole genome sequencing (WGS).

ODC Protein Expression and Polyanines in Red Blood Cells

RBC lysates were analyzed by SDS-PAGE and Western blot using commercially available ODC and GAPDH antibodies (Santa Cruz Biotechnology). Blots were imaged using an Odyssey Clx (Licor) Western blot scanner. PA from RBCs and plasma were analyzed by HPLC as previously described.[6,7] In some embodiments, polyamines are measured in serum. In some embodiments, polyamines are measured in urine.

Molecular Modeling

Molecular models with human ODC were rendered using Visual Molecular Dynamics (VMD) (http://www.ks.uiuc.edu/Research/vmd/) by utilizing the published crystal structure of human ODC (cyan) in complex with a c-terminal fragment of antizyme (red) (PDB ID: 4ZGY).[8-11] For a detailed protocols, see Supplementary Methods.

SDS-PAGE and Western Blot

RBC lysates were prepared in radioimmunoprecipitation assay (RIPA) buffer supplemented with complete protease inhibitor cocktail (Roche Molecular Biochemicals), and phosphatase inhibitors. Total protein concentration was determined using the Bradford dye reagent protein assay (Bio-Rad Laboratories). Cell lysates in SDS sample buffer were boiled for 10 minutes and equal amounts of protein were resolved by 10% SDS-PAGE. Protein was electrotransferred onto 0.45 µM polyvinylidene difluoride Immobilon-P membrane (Millipore). ODC and GAPDH antibodies (Santa Cruz Biotechnology) were incubated overnight at 4° C. in 5% BSA in Tris-buffered saline containing 0.1% Tween-20. Secondary antibodies were incubated for 1 hour at room temperature in Tris-buffered saline containing 0.1% Tween-20. Blots were imaged using an Odyssey Clx (Licor) Western blot scanner.

Polyamine Analysis

Polyamines (PA) from RBCs and plasma were isolated, dansylated, and analyzed by reverse-phase HPLC. Briefly, PA were extracted and protonated in perchloric acid/sodium chloride buffer. To each sample, 4.5 nmol of 1,7 diaminoheptane internal standard was added prior to dansylation with 400 µl of 5 mg/ml dansyl chloride (Sigma Aldrich). Samples were analyzed using a Thermo Scientific/Dionex Ultimate 3000 HPLC equipped with a Syncronis C18 column (250×4.6 mm, 5 µM pore size). The dansylated polyamine derivatives were visualized by excitation at 340 nM and emission at 515 nM. Using the relative molar response derived from N-dansylated polyamine and 1,7 diaminoheptane standards, the amount of N-dansylated polyamine derivatives was calculated and normalized to red blood cell number or starting plasma volume. In some embodiments, polyamines are isolated from urine.

Molecular Modeling

Molecular models with human ODC were rendered using Visual Molecular Dynamics (VMD) (http://www.ks.uiuc.edu/Research/vmd/). The molecular model was rendered by utilizing the published crystal structure of human ODC (cyan) in complex with a c-terminal fragment of antizyme (red) (PDB ID: 4ZGY). The c-terminus portion of the protein extends from amino acid (aa) residues 376 to 461. The mobile nature of the c-terminal destabilization region (aa 425 to 461) prevented its crystallization and, therefore, has been marked with a dashed purple line. The ODC1 patient's deleted region at the c-terminus of ODC (aa 448-461) has been marked with a dashed green line.

Results

The patient was born at 37 weeks gestation by C-section for failure to progress. Apgar scores were 3 and 7. Birthweight was 3.5 kg (62% ile), length was 54 cm (96% ile), and head circumference was 38 cm (97% ile). The pregnancy was complicated by flu like illness at 27 weeks gestation, decreased fetal movement, and polyhydramnios. Neonatal intensive care was required for 35 days due to hypotonia, hypoglycemia, feeding difficulties, and hyperbilirubinemia. A G-tube was placed for feeding support. She failed the newborn hearing screen and was diagnosed with right-sided sensorineural hearing loss. She was born with copious silver/blonde-colored hair, which fell out during the first month of life leaving her bald (FIG. 1). She also had no eyebrows and few eyelashes congenitally. Physical exam was notable for erythematous vascular marking on the posterior head and neck (FIG. 1c). Subcutaneous vasculature on her scalp became more prominent over time and her head consistently felt warmer to the touch (FIGS. 1c and d). She had cupped ears and high arched palate.

At 11 months of age, developmental delay was noted. She had poor neck control with only cooing and babbling. At 30 months of age she remained nonverbal still only making cooing noises with occasional imitation of sounds. She was unable to sit unsupported, could consistently roll back to front but not always front to back, and had gross reach without pincer grasp. She developed spasticity in the lower extremities requiring orthoses. She had episodes of nighttime eye deviation and tonic deviation of the limbs occurring one to two times per week, typically within 2 hours of falling asleep. No EEG evidence of seizures was noted. Family history was noncontributory.

Neurology was consulted and the diagnostic evaluation included serum levels of very long chain fatty acids, serum pipecolic acid, 7-deoxydrocholesterol, serum amino acids, urine organic acids, and serum ammonia, all of which were normal. Ophthalmology assessment noted intermittent esotropia, pseudostrabismus, and myopic astigmatism bilaterally. She did not exhibit subsequent increased susceptibility to infectious diseases or require further hospitalizations. Primary teeth erupted rapidly but appeared normal. Nails had exaggerated curve and were brittle when cut. She had normal wound healing but had quite high tolerance for pain. At 3 years of age her height remained between 50-75% ile for age, weight 10-50% ile, and head circumference 90-97% ile. The MRI performed on day 2 of life due to macrocephaly showed prominent cystic changes in the periventricular region. Subsequent brain MRI performed at 15 months of age showed resolution of previous periventricular cystic change but progression of white matter volume loss in both cerebral hemispheres and lateral ventricles were enlarged likely secondary to white matter volume loss. A summary of phenotypic manifestations observed in this first patient are listed in Table 2.

Whole-genome array CGH was initially performed and returned normal. Whole-exome sequencing trio was subsequently completed. One mutation in DHCR7, which is associated with the autosomal recessive disorder Smith-Lemli-Opitz syndrome, was identified on the exome, but biochemical testing (7-dehydrocholesterol level) done in follow-up was normal, excluding this diagnosis. A de novo ODC1 mutation was identified (c.1342 A>T) which introduces a stop codon, leading to premature abrogation and deletion of the c-terminal 14 aa of the ODC protein (p.K448X). ODC1 is located on chromosome 2p25.1 (FIG. 2a-c).

Figure 2:
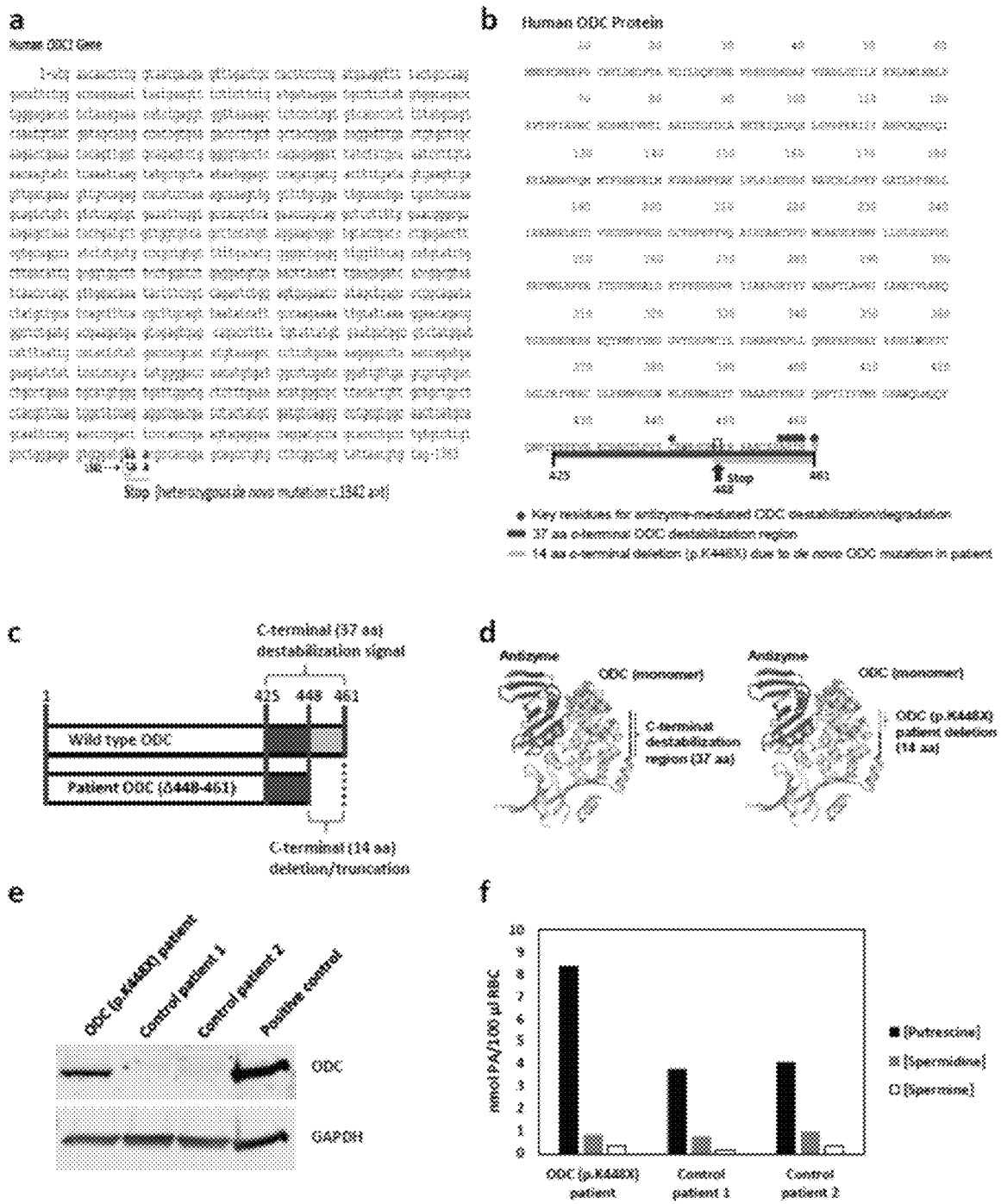
FIG. 2 consists of six parts, Parts A through F, and shows the location and functional characterization of a de novo mutation in ODC1 in a pediatric patient with distinct clinical features. Open reading frame (ORF) of human ODC1 gene (1-1383 bp) (SEQ ID NO: 1), depicting the heterozygous de novo mutation of patient (c.1342 A>T) (SEQ ID NO: 2) converting 'AAA' (lysine codon) to 'TAA' (stop codon) (Part A). Human ODC protein sequence (aa 1-461) (SEQ ID NO: 3), indicating the site at which lysine is converted into a stop signal (p.K448X) (Part B). Premature abrogation of protein translation produces a 14-aa truncation at the c-terminus of ODC (green line). This deletion lies within the 37-aa destabilization region and contains key residues that contribute to ODC destabilization (Part C). Crystal structure of ODC in complex with antizyme (PDB ID: 4ZGY). Antizyme binds ODC and, through a conformational change, engages the ODC c-terminus to induce ubiquitin-independent proteasomal degradation (Part D). The ODC monomer is depicted in cyan, and the bound antizyme is shown in red. The c-terminal portion of the ODC protein extends from aa 376-461. Due to the mobile nature of aa 425 to 461, the crystal structure of the c-terminal destabilization region has not been solved and the predictive modeling software failed to produce a structure for this region. The 37-aa destabilization region (purple) and the 14-aa region (green) which is deleted in the patient are marked with dashed lines (Part D). ODC is a rapid-turnover enzyme but without its c-terminus, antizyme binding does not induce ODC proteasomal degradation which leads to a more stable but active ODC protein that accumulates in cells. Western blotting of ODC, with the use of an antibody that reacts with human ODC, in red blood cell (RBC) lysates shows that ODC protein is accumulated in RBCs from the female patient but is absent (or present only at undetectable levels) in cells from two normal control patients 1 and 2 (see Materials and Methods for control description) (Part D) Lysates from neuroblastoma cells with high ODC expression were used as positive control. Glyceraldehyde-3-phosphate dehydrogenase (GAPDH) was used to show equal loading of the protein in all samples. High-performance liquid chromatography (HPLC) was used to separate and detect standard PA (putrescine, spermidine, spermine) in RBCs (Part F). The data represents the average PA levels of each patient's RBC sample processed and analyzed three times. Putrescine was elevated 2.2-fold and 2.1-fold in RBCs from the patient compared to two normal controls 1 and 2, respectively. No significant changes in spermidine and spermine levels were observed.

Several previous in vitro studies established that the c-terminal 37 aa of ODC represent a key destabilization region (purple line) that is pivotal for antizyme-mediated and ubiquitin-independent proteasomal degradation of ODC and key residues are highlighted (purple dots) (FIG. 2b).[10-14] Deletion of the 37-aa destabilization region has been shown to render a more stable ODC protein (longer half-life) that exhibits higher ODC enzyme activity, compared to the wild type ODC protein (FIG. 2c).[15] Using the x-ray structure of ODC complexed with antizyme, two molecular models highlighting the 37-aa destabilization region (left) and the location of the c-terminal 14-aa deletion (right) were generated, introduced by the p.K448X mutation as identified in the patient (FIG. 2d). Importantly, in vivo studies with a transgenic mouse that expresses a c-terminal 34 aa deletion (aa 428-461) using a specific promoter targeted to the skin confirmed that the truncation of the ODC c-terminus produces a more stable protein.[16; 17] These heterozygous mice had elevated ODC protein and increased polyamine (mostly putrescine) levels, and importantly, presented with phenotypic manifestations that include multiple skin and hair follicle abnormalities and alopecia,[16; 17] symptoms similar to those also identified in the patient (Table 2). Strikingly, the phenotypic changes in these mice were reversible with ODC inhibitor alpha-difluoromethylornithine (DFMO; eflornithine),[17] a FDA-approved drug effective in patients with African sleeping sickness (trypanosomiasis) that is also studied as a therapeutic and chemopreventive agent in clinical trials for pediatric neuroblastoma and colon cancer patients.[18-20] Combination therapies comprising DFMO for the treatment of tumors can be found in U.S. Pat. No. 9,072,778, hereby incorporated by reference in its entirety. Importantly, other mouse models have since been developed that overexpress full-length ODC protein in multiple tissues using very strong promoters or high gene copy numbers, and these mice also produce high levels of putrescine.[21]

To verify if the patient expresses higher ODC and polyamine levels, RBCs and blood serum of the patient and two healthy controls were analyzed for ODC protein and polyamine levels by Western blot and high performance liquid chromatography (HPLC), respectively (FIGS. 2e and f). It was found that the ODC protein level was clearly increased in RBCs of the patient compared to two age/gender-matched controls (FIG. 2e). Ornithine is enzymatically converted to putrescine by the action of ODC, and higher ODC levels are expected to yield higher levels of putrescine. Indeed, putrescine levels were substantially increased in RBCs compared to two controls, thus further suggesting that ODC is accumulated in the patient (FIG. 2f). Spermidine and spermine are downstream metabolic products of putrescine in the polyamine biosynthetic pathway and did not significantly change. Polyamine levels in blood plasma did not change (not shown). Of note, previous studies showed that in healthy children (age ≥3) putrescine levels in the blood are quite low and steady throughout adulthood. In contrast, spermidine and spermine levels vary significantly as age progresses, with highest levels shortly after birth and lowest levels in adulthood.[22]

Discussion

In this study, a new autosomal dominant genetic disorder caused by a heterozygous de novo mutation in the ODC1 gene was identified. ODC1 encodes for ODC, a rate-limiting enzyme in the biosynthesis of PA (putrescine, spermidine, spermine). PA are polycationic molecules that engage in a range of physiological and cell developmental processes including both normal and neoplastic cell proliferation.[1-5] This new syndrome is linked to a gain-of-function mutation in the ODC1 gene and characterized by macrosomia, macrocephaly, developmental delay, alopecia, spasticity, hypotonia, cutaneous vascular malformation, delayed visual maturation, and sensorineural (unilateral) hearing loss (Table 2).

TABLE 2

Summary of major clinical manifestations of patient with c-terminal ODC truncation (p.K448X) Symptoms Macrosomia
Macrocephaly
Developmental delay
Alopecia (develops over time)
Spasticity
Hypotonia
Cutaneous vascular malformation
Delayed visual maturation
Sensorineural hearing loss (unilateral)

A 32-months old female patient was diagnosed and identified a de novo nonsense mutation in ODC1 (c.1342 A>T) which introduced a stop codon (p.K448X), leading to premature abrogation and deletion of the c-terminal 14 aa of the ODC protein. The patient had elevated ODC protein levels in RBCs and increased PA putrescine levels compared to two controls.

The c-terminus of ODC is of high functional importance and contains a 37-aa protein destabilization region.[10-14] In vitro, the deletion of this region leads to a more stable ODC protein with reduced degradation and retained enzymatic function.[15] Remarkably, Tom O'Brien and colleagues demonstrated over 20 years ago that transgenic mice overexpressing c-terminally deleted ODC (p.P427X) expressed more stable ODC that led to higher enzyme activity and increased polyamine metabolism.[16; 17] These transgenic mice presented with phenotypic manifestations that include skin, nail, and hair follicle abnormalities, symptoms comparable with those observed in the patient. Skin abnormalities included increasingly wrinkled and folded skin as the animals aged due to the increase in size and the number of dermal pilar and follicular cysts. First morphological changes appeared about twelve days after birth. At that time, mice began to exhibit progressive hair loss, including vibrissae, which was complete by 6 weeks of age. In addition, they displayed irreversible alopecia and nail growth was also accelerated. Off-spring from six different founders all displayed the same phenotypic manifestations, strongly confirming the reproducibility of this observation.

Incidentally, increased activity of spermidine/spermine N(1)-acetyltransferase (SSAT) also leads to putrescine accumulation and the development of keratosis follicularis spinulosa decalvans (KFSD) in a patient with SSAT gene duplication.[23] Like ODC, SSAT is an important rate-limiting enzyme that acts in the catabolic pathway of PA metabolism through its involvement in PA acetylation and re-conversion of spermine to spermidine and spermidine to putrescine. Furthermore, SSAT overexpressing transgenic mice present with a hairless phenotype and dermal cysts instead of hair follicles[21], thus further confirming the importance of putrescine in the development of these clinical manifestations.

Most intriguingly, the ODC inhibitor DFMO, a water soluble, FDA-approved drug, which blocks putrescine production, prevented hair loss and also partially restored hair growth in mice with complete hair loss. Moreover, DFMO also activated reappearance of normal follicles in mice. DFMO has been used for many years in the treatment of trypanosomiasis and more recently entered clinical trials for pediatric neuroblastoma and colon cancer.[18-20] Overall, DFMO is considered a well-tolerated drug and its efficacy in the murine model of this disease may justify its use in non-life-threatening conditions such as the herein described new syndrome (Table 2).

In conclusion, this is the first case reported of a human patient with a c-terminal ODC1 deletion that presents with a new pediatric developmental disorder. ODC1 mutation leads to an increase of ODC protein and polyamine levels, suggesting gain-of-function. DFMO may serve as a disease-modifying drug and an early therapeutic trial in a new diagnosis may prevent some the herein described features and possibly slow the neurologic deterioration as the patient grows older.

REFERENCES

1. Casero, R. A., Jr., and Marton, L. J. (2007). Targeting polyamine metabolism and function in cancer and other hyperproliferative diseases. Nat Rev Drug Discov 6, 373-390.
2. Gerner, E. W., and Meyskens, F. L., Jr. (2004). Polyamines and cancer: old molecules, new understanding. Nat Rev Cancer 4, 781-792.
3. Pegg, A. E. (2016). Functions of Polyamines in Mammals. J Biol Chem 291, 14904-14912.
4. Pegg, A. E., and McCann, P. P. (1982). Polyamine metabolism and function. Am J Physiol 243, C212-221.
5. Wallace, H. M., Fraser, A. V., and Hughes, A. (2003). A perspective of polyamine metabolism. Biochem J 376, 1-14.
6. Minocha, S. C., Minocha, R., and Robie, C. A. (1990). High-performance liquid chromatographic method for the determination of dansyl-polyamines. J Chromatogr 511, 177-183.
7. Schultz, C. R., Geerts, D., Mooney, M., El-Khawaja, R., Koster, J., and Bachmann, A. S. (2018). Synergistic drug combination GC7/DFMO suppresses hypusine/spermidine-dependent eIF5A activation and induces apoptotic cell death in neuroblastoma. Biochem J 475, 531-545.
8. Almrud, J. J., Oliveira, M. A., Kern, A. D., Grishin, N. V., Phillips, M. A., and Hackert, M. L. (2000). Crystal structure of human ornithine decarboxylase at 2.1 A resolution: structural insights to antizyme binding. J Mol Biol 295, 7-16.
9. Humphrey, W., Dalke, A., and Schulten, K. (1996). VMD: visual molecular dynamics. J Mol Graph 14, 33-38, 27-38.
10. Li, X., and Coffino, P. (1993). Degradation of ornithine decarboxylase: exposure of the C-terminal target by a polyamine-inducible inhibitory protein. Mol Cell Biol 13, 2377-2383.
11. Wu, H. Y., Chen, S. F., Hsieh, J. Y., Chou, F., Wang, Y. H., Lin, W. T., Lee, P. Y., Yu, Y. J., Lin, L. Y., Lin, T. S., et al. (2015). Structural basis of antizyme-mediated regulation of polyamine homeostasis. Proc Natl Acad Sci USA 112, 11229-11234.
12. Takeuchi, J., Chen, H., Hoyt, M. A., and Coffino, P. (2007). Structural elements of the ubiquitin-independent proteasome degron of ornithine decarboxylase. Biochem J.
13. Wu, D., Kaan, H. Y., Zheng, X., Tang, X., He, Y., Vanessa Tan, Q., Zhang, N., and Song, H. (2015). Structural basis of Ornithine Decarboxylase inactivation and accelerated degradation by polyamine sensor Antizyme1. Sci Rep 5, 14738.
14. Zhang, M., Pickart, C. M., and Coffino, P. (2003). Determinants of proteasome recognition of ornithine decarboxylase, a ubiquitin-independent substrate. Embo J 22, 1488-1496.
15. Ghoda, L., van Daalen Wetters, T., Macrae, M., Ascherman, D., and Coffino, P. (1989). Prevention of rapid intracellular degradation of ODC by a carboxyl-terminal truncation. Science 243, 1493-1495.
16. Megosh, L., Gilmour, S. K., Rosson, D., Soler, A. P., Blessing, M., Sawicki, J. A., and O'Brien, T. G. (1995). Increased frequency of spontaneous skin tumors in transgenic mice which overexpress ornithine decarboxylase. Cancer Res 55, 4205-4209.
17. Soler, A. P., Gilliard, G., Megosh, L. C., and O'Brien, T. G. (1996). Modulation of murine hair follicle function by alterations in ornithine decarboxylase activity. J Invest Dermatol 106, 1108-1113.
18. Meyskens, F. L., Jr., McLaren, C. E., Pelot, D., Fujikawa-Brooks, S., Carpenter, P. M., Hawk, E., Kelloff, G., Lawson, M. J., Kidao, J., McCracken, J., et al. (2008). Difluoromethylornithine plus sulindac for the prevention of sporadic colorectal adenomas: a randomized placebo-controlled, double-blind trial. Cancer Prev Res (Phila Pa.) 1, 32-38.
19. Priotto, G., Kasparian, S., Mutombo, W., Ngouama, D., Ghorashian, S., Arnold, U., Ghabri, S., Baudin, E., Buard, V., Kazadi-Kyanza, S., et al. (2009). Nifurtimox-eflornithine combination therapy for second-stage African *Trypanosoma brucei* gambiense trypanosomiasis: a multicentre, randomised, phase III, non-inferiority trial. Lancet 374, 56-64.
20. Saulnier Sholler, G. L., Gerner, E. W., Bergendahl, G., MacArthur, R. B., VanderWerff, A., Ashikaga, T., Bond, J. P., Ferguson, W., Roberts, W., Wada, R. K., et al. (2015). A Phase I Trial of DFMO Targeting Polyamine Addiction in Patients with Relapsed/Refractory Neuroblastoma. PLoS One 10, e0127246.
21. Janne, J., Alhonen, L., Pietila, M., and Keinanen, T. A. (2004). Genetic approaches to the cellular functions of polyamines in mammals. Eur J Biochem 271, 877-894.
22. Casti, A., Orlandini, G., Reali, N., Bacciottini, F., Vanelli, M., and Bernasconi, S. (1982). Pattern of blood polyamines in healthy subjects from infancy to the adult age. J Endocrinol Invest 5, 263-266.
23. Gimelli, G., Giglio, S., Zuffardi, O., Alhonen, L., Suppola, S., Cusano, R., Lo Nigro, C., Gatti, R., Ravazzolo, R., and Seri, M. (2002). Gene dosage of the spermidine/spermine N(1)-acetyltransferase (SSAT) gene with putrescine accumulation in a patient with a Xp21.1p22.12 duplication and keratosis follicularis spinulosa decalvans (KFSD). Hum Genet 111, 235-241.

INCORPORATION BY REFERENCE

All publications, including but not limited to patents and patent applications, cited in this specification, to the extent that they provide exemplary procedural or other details supplementary to those set forth herein, are specifically incorporated herein by reference as if each individual publication were specifically and individually indicated to be incorporated by reference herein as though fully set forth.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A method of treating a developmental disorder associated with a mutation in the ODC1 gene which increases levels of a polyamine in a human subject comprising administering to the subject at least one agent that inhibits the expression and/or activity of the mutant ODC1 gene product;

wherein the mutation is c.1342 A>T; and
wherein the agent is eflornithine (DFMO).

2. The method of claim 1, wherein the developmental disorder is characterized by macrosomia, macrocephaly, developmental delay, alopecia, spasticity, hypotonia, cutaneous vascular malformation, delayed visual maturation, or sensorineural hearing loss.

* * * * *